(12) United States Patent
Katsuki et al.

(10) Patent No.: US 8,425,841 B2
(45) Date of Patent: *Apr. 23, 2013

(54) ANALYZING INSTRUMENT

(75) Inventors: Koji Katsuki, Kyoto (JP); Tetsuya Sakata, Kyoto (JP); Yasunori Shiraki, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/902,647

(22) Filed: Oct. 12, 2010

(65) Prior Publication Data

US 2011/0060203 A1    Mar. 10, 2011

Related U.S. Application Data

(63) Continuation of application No. 10/484,955, filed as application No. PCT/JP02/07654 on Jul. 26, 2002, now Pat. No. 7,824,616.

(30) Foreign Application Priority Data

Jul. 27, 2001 (JP) .................................. 2001-227777
Aug. 9, 2001 (JP) .................................. 2001-242486

(51) Int. Cl.
*A61B 5/157* (2006.01)
*A61B 5/00* (2006.01)

(52) U.S. Cl.
USPC ............ 422/68.1; 422/50; 600/345; 600/309; 600/300

(58) Field of Classification Search ................. 422/68.1, 422/50; 600/345, 309, 300
See application file for complete search history.

(56) References Cited

U.S. PATENT DOCUMENTS

| 4,452,887 A | 6/1984 | Kitajima et al. ................. 435/14 |
| 4,790,640 A | 12/1988 | Nason ............................ 350/534 |
| 4,849,340 A * | 7/1989 | Oberhardt ........................ 435/13 |

(Continued)

FOREIGN PATENT DOCUMENTS

| DE | 43 07 735 A1 | 9/1993 |
| DE | 19753850 A1 | 6/1999 |

(Continued)

OTHER PUBLICATIONS

Wettabilty definition. Webpage from http://www.attension.com/wettabilty.aspx. Download Date:Oct. 19, 2011. Two pages.*

(Continued)

*Primary Examiner* — Christine T Mui
(74) *Attorney, Agent, or Firm* — Morgan, Lewis & Bockius LLP

(57) ABSTRACT

The present invention relates to an analyzing instrument (X1) provided with a capillary (5) for moving a sample liquid. The analyzing instrument (X1) includes a dehumidification region for maintaining a constant moisture content in the capillary (5). Preferably, the dehumidification region has a hygroscopicity of no less than 2%. Preferably, at least part of an inner surface of the capillary (5) extends in the moving direction of the sample liquid and is a water-insoluble high-wettability region having a wettability of no less than 57 mN/m. The dehumidification region and the high-wettability region may be made of Vinylon, for example. Preferably, the analyzing instrument (X1) includes a liquid pooling portion (4) communicating with the capillary (5) and having a portion wider than the capillary (5).

30 Claims, 16 Drawing Sheets

U.S. PATENT DOCUMENTS

| | | | | |
|---|---|---|---|---|
| 5,399,316 | A | 3/1995 | Yamada | 422/58 |
| 5,575,895 | A | 11/1996 | Ikeda et al. | 204/403 |
| 5,759,364 | A * | 6/1998 | Charlton et al. | 204/403.14 |
| 5,872,713 | A | 2/1999 | Douglas et al. | 364/413.09 |
| 5,879,311 | A | 3/1999 | Duchon et al. | 600/583 |
| 5,951,492 | A | 9/1999 | Douglas et al. | 600/583 |
| 5,951,493 | A | 9/1999 | Douglas et al. | 600/583 |
| 5,975,153 | A | 11/1999 | Hill et al. | 141/31 |
| 5,997,817 | A | 12/1999 | Crismore et al. | 422/58 |
| 6,001,307 | A * | 12/1999 | Naka et al. | 422/81 |
| 6,015,392 | A | 1/2000 | Douglas et al. | 600/583 |
| 6,048,352 | A | 4/2000 | Douglas et al. | 606/181 |
| 6,056,701 | A | 5/2000 | Duchon et al. | 600/583 |
| 6,071,250 | A | 6/2000 | Douglas et al. | 600/583 |
| 6,071,251 | A | 6/2000 | Cunningham et al. | 600/584 |
| 6,099,484 | A | 8/2000 | Douglas et al. | 600/583 |
| 6,106,780 | A | 8/2000 | Douglas et al. | 422/58 |
| 6,183,489 | B1 | 2/2001 | Douglas et al. | 606/181 |
| 6,214,185 | B1 | 4/2001 | Offenbacher et al. | 204/403 |
| 6,254,736 | B1 | 7/2001 | Earl et al. | 204/164 |
| 6,270,637 | B1 | 8/2001 | Crismore et al. | 204/403 |
| 6,319,210 | B1 | 11/2001 | Douglas et al. | 600/583 |
| 6,332,871 | B1 | 12/2001 | Douglas et al. | 600/583 |
| 6,352,514 | B1 | 3/2002 | Douglas et al. | 600/583 |
| 6,447,657 | B1 | 9/2002 | Bhullar et al. | 204/409 |
| 6,540,890 | B1 | 4/2003 | Bhullar et al. | 204/403.02 |
| 6,662,439 | B1 | 12/2003 | Bhullar | 29/825 |
| 6,767,440 | B1 | 7/2004 | Bhullar et al. | 204/403.01 |
| 6,780,651 | B2 | 8/2004 | Douglas et al. | 436/518 |
| 7,008,799 | B1 | 3/2006 | Zimmer et al. | 436/514 |
| 7,025,836 | B1 | 4/2006 | Zimmer et al. | 148/277 |
| 7,238,534 | B1 | 7/2007 | Zimmer | 436/169 |
| 7,824,616 | B2 * | 11/2010 | Katsuki et al. | 422/68.1 |
| 2004/0171968 | A1 | 9/2004 | Katsuki et al. | 600/583 |
| 2007/0266803 | A1 | 11/2007 | Zimmer | |

FOREIGN PATENT DOCUMENTS

| | | |
|---|---|---|
| EP | 0 435 246 A2 | 7/1991 |
| EP | 8803288 A2 | 10/1997 |
| EP | 0 924 520 A2 | 6/1999 |
| EP | 1 156 325 | 11/2001 |
| EP | 1 174 716 | 1/2002 |
| JP | 2-95352 | 4/1990 |
| JP | 6-229970 | 8/1994 |
| JP | 7-55793 | 3/1995 |
| JP | 7-55795 | 3/1995 |
| JP | 8-50113 | 2/1996 |
| JP | 9-266898 | 10/1997 |
| JP | 11-304748 | 11/1999 |
| JP | 11-347018 | 12/1999 |
| JP | 2000-221121 | 8/2000 |
| JP | 2000-258382 | 9/2000 |
| JP | 2001-159618 | 6/2001 |
| JP | 2001-526388 | 12/2001 |
| WO | WO 99/30152 | 6/1999 |
| WO | 99/41147 A1 | 8/1999 |
| WO | WO 00/40150 | 7/2000 |
| WO | WO 01/73395 A2 | 10/2001 |

OTHER PUBLICATIONS

Trojanowicz, M.; Krawczyfiski vel Krawczyk, T. "Electrochemical Biosensors Based on Enzymes Immobilized in Electropolymerized Films." Mikrochim. Acta 1995, 121, pp. 167-181.

Doretti, L.; Ferrara, D.; Gattolin, P.; Lora, S. "Amperometric biosensor with physically immobilized glucose oxidase on a PVA cryogel membrane." Talanta, 1997, 44, pp. 859-866.

Extended European Search Report issued in corresponding European Patent Application No. 10193213.5 dated Jan. 26, 2012.

* cited by examiner

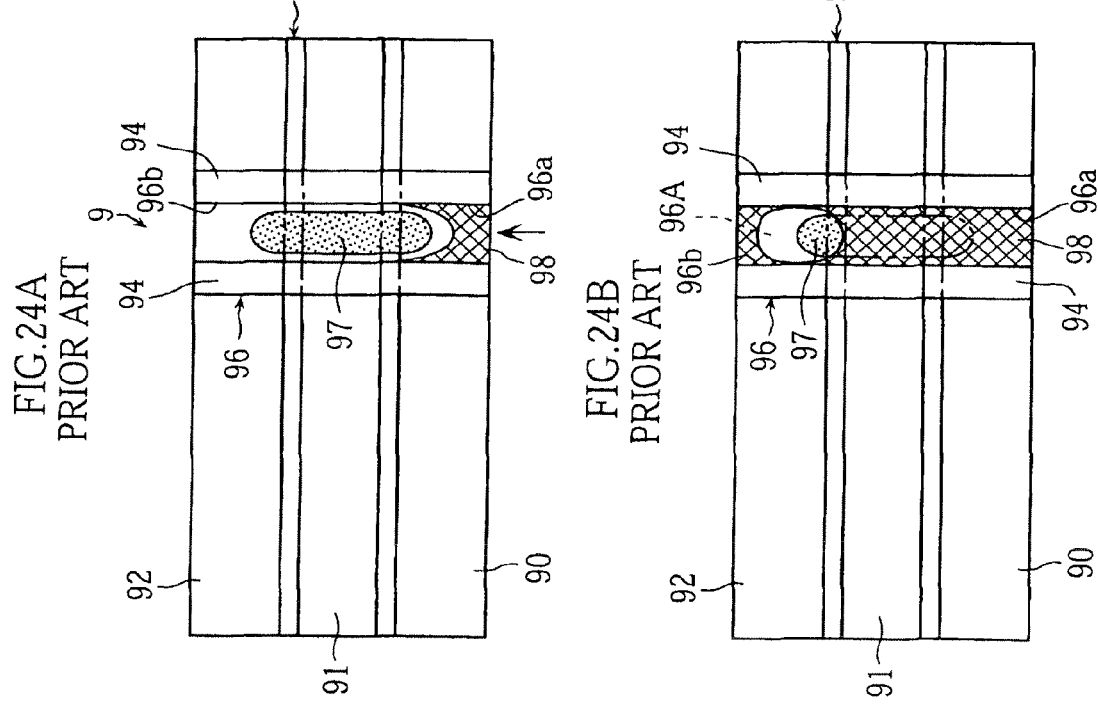
FIG.24A PRIOR ART
FIG.24B PRIOR ART
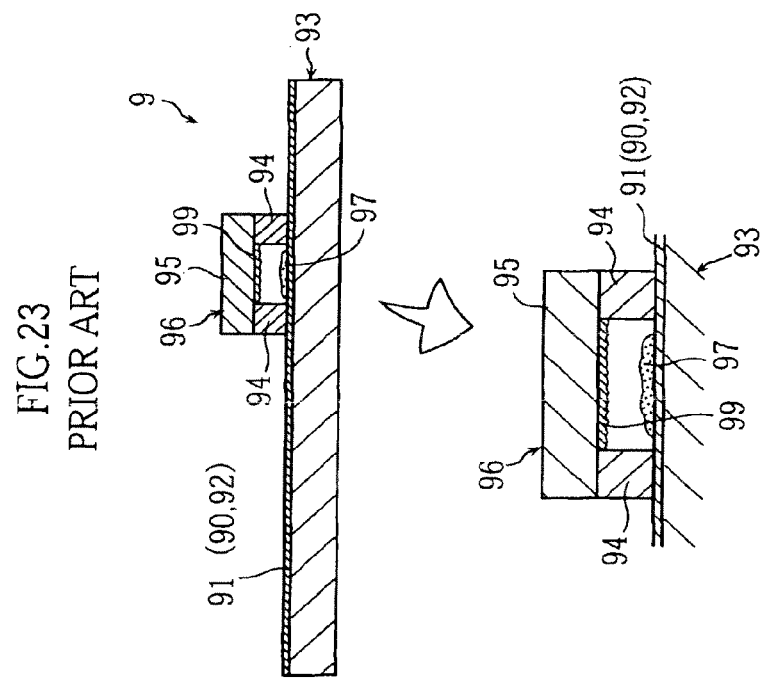
FIG.23 PRIOR ART

ANALYZING INSTRUMENT

This application is a continuation of prior application Ser. No. 10/484,955, filed Jan. 27, 2004, now U.S. Pat. No. 7,824,616, which is a national stage application of PCT/JP02/07654 filed Jul. 26, 2002, which claims priority to Japanese Application 2001-227777 filed Jul. 27, 2001 and Japanese Application 2001-242486 filed Aug. 9, 2001, all of which are hereby incorporated by reference.

TECHNICAL FIELD

The present invention relates to an analyzing instrument to be mounted to a concentration measuring apparatus for measuring the concentration of a particular component in a sample liquid.

BACKGROUND ART

Redox reaction is generally utilized for measuring the concentration of a particular component in a body fluid, such as the concentration of glucose in blood. On the other hand, portable hand-held blood glucose level measuring apparatuses are available so that diabetics can easily measure the blood glucose level at home or away from home. For measuring the blood glucose level using such a portable blood glucose level measuring apparatus, a disposable biosensor for providing an enzyme reaction system is mounted to the blood glucose level measuring apparatus, and blood is supplied to the biosensor. Recently, to reduce the burden on the diabetics, a blood glucose level measuring apparatus integrated with a lancet has been developed so that lancing of the skin with a lancet and introduction of blood from the skin to the biosensor can be performed in immediate succession.

Various biosensors have been put to practical use, and an example of such biosensors is shown in FIGS. 23 and 24A. The illustrated biosensor 9 comprises a substrate 93 having an upper surface formed with a counterpart electrode 90, an operative electrode 91 and a reference electrode 92 each in the form of a strip, and a cover 95 laminated on the substrate via a pair of spacers 94. The substrate 93, the spacers 94 and the cover 95 define a capillary 96. The capillary 96 includes end openings 96a, 96b, and a reagent layer 97 in a solid state extending transversely over the counterpart electrode 90, the operative electrode 91 and the reference electrode 92. The reagent layer 97 contains oxidoreductase and an electron carrier. The cover 95 has an inner surface provided with a hydrophilic layer 99 formed by applying a surface-active agent such as lecithin. The hydrophilic layer 99 is provided to cause highly viscous blood (high Hct value) to properly move through the capillary 96.

In the biosensor 9, blood 98 is introduced through one opening 96a, as shown in 24A. The blood 98 travels through the capillary 96 toward the other opening 96b by capillary action under the assisting action of hydrophilic layer 99 while dissolving the reagent layer 97. In the reagent layer 97, oxidoreductase oxidizes glucose in the blood while reducing the electron carrier. When a potential is applied across the operative electrode 91 and the counterpart electrode 90, the electron carrier is oxidized (releases electrons). The blood glucose level measuring apparatus measures an oxidation current. The glucose concentration is figured out based on the oxidation current.

However, due to the provision of the openings 96a and 96b at the opposite ends of the capillary 96, the reagent layer 97 may be exposed to water entering the capillary 96 through the openings 96a and 96b if such water exists around the biosensor 9 during the storage thereof. Specifically, even when the blood 98 is not introduced into the capillary 96, water reduces the electron carrier. Therefore, not only the electrons released due to the reaction with glucose but also the water-induced electrons are detected as oxidation current. Such background current (noise) by the electrons due to water results in measurement errors. Moreover, since the solubility of the reagent layer 97 changes in accordance with the hygroscopicity, the time taken for filling the capillary with blood (suction time) cannot be kept constant, which causes difficulty in proper measurement.

Since the hydrophilic layer 99 is provided by applying a surface-active agent dissolved in an organic solvent to the cover 95 and then drying, the surface-active agent is easily removed from the cover. When the surface-active agent is removed from the cover 95, the region from which the surface-active agent has been removed has a low wettability, which causes a low travel speed. Further, the surface-active agent thus removed may move through the capillary 96 together with the blood 98 (particularly blood cells). While the hydrophilic surface-active agent is likely to move through a hydrophobic portion, the spacers 94 are made of a hydrophobic double-sided tape or fixed to the substrate 93 and the cover 95 with a hydrophobic double-sided tape. Therefore, as shown in FIG. 24A, the blood moves faster along the spacers 94 than along the inner surface of the cover 95. Thus, variation is caused in the speed distribution of the blood flow in the capillary 96.

When such a phenomenon occurs, spreading of the blood entirely over the reagent layer 97 takes a long time. Therefore, when oxidation current is to be measured at a predetermined time after the blood introduction, the reagent layer 97 may not have been completely dissolved at the time of the measurement. Further, as shown in FIG. 24B, the blood flowing along the spacers 94 may sometimes reach the opening 96b earlier than blood flowing along other portions and may close the opening 96b to hinder the movement of the blood 98, thereby producing an air stagnating portion 96A in the capillary 96. When the air stagnating portion 96A is produced, the reagent layer 97 at the air stagnating portion 96A is not dissolved. In this way, variation in the speed distribution of the blood flow hinders sufficient dissolving of the reagent layer 97 within a predetermined time, which may increase the measurement errors and deteriorate the reproducibility.

When a blood glucose level measuring apparatus which is not provided with a lancet is used, a lancet disclosed in JP-A-9-266898, for example, may be used for introducing blood to the biosensor 9. In using the lancet, it is necessary to lance the skin with the lancet and bring the blood from the skin into contact with the opening 96a of the biosensor 9.

At that time, the user needs to perform the operation carefully while visually confirming the contact of blood with the opening 96a. Further, in the biosensor 9, blood need be introduced after it is confirmed that the amount of blood needed for the measurement is extracted from the skin, because otherwise, the amount of blood introduced to the biosensor 9 may be insufficient or the time taken for filling the capillary with the blood after the starting of the blood introduction is not kept constant.

In this way, the use of the biosensor 9 for a blood glucose level measuring apparatus which is not provided with a lancet involves a large burden on the user. Since the burden on the eyes is particularly large, the use is very difficult for a person who has weak eyesight due to the progress of diabetes, and the measurement accuracy is likely to be deteriorated.

In the case where the biosensor 9 is used for a blood glucose level measuring apparatus provided with a lancet, the arrangement for automatically bringing the blood from the skin into contact with the small opening 96a cannot be realized due to various technical difficulties in terms of the positioning of the biosensor 9 and the timing of contacting, for example.

DISCLOSURE OF THE INVENTION

An object of the present invention is to provide an analyzing instrument capable of properly supplying a sample liquid to a capillary and accurately measuring the concentration of a target component in the sample liquid.

According to a first aspect of the present invention, there is provided an analyzing instrument provided with a capillary for moving a sample liquid. The analyzing instrument includes a dehumidification region for maintaining moisture content in the capillary.

The inside of the capillary communicates with the outside through a first opening and a second opening, and the dehumidification region is provided adjacent to at least one of the first opening and the second opening or on at least part of an inner surface of the capillary.

For example, a reagent layer may be disposed in the internal space, whereby the analyzing instrument of the present invention may be constituted as a biosensor.

Preferably, the dehumidification region has a hygroscopicity of no less than 2%. Preferably, at least part of an inner surface of the capillary extends in the moving direction of the sample liquid and is a water-insoluble high-wettability region having a wettability of no less than 57 mN/m.

Herein, the hygroscopicity is determined pursuant to ASTM D570, whereas the wettability is determined according to JIS K6768.

Preferably, the capillary may be formed by laminating a cover on a substrate, and at least part of the cover may be made of Vinylon.

Preferable examples of Vinylon include one whose degree of saponification is no less than 95% (preferably no less than 99%), one whose degree of acetalization is 30-40%, or one whose degree of saponification is no less than 95% (preferably no less than 99%) and whose degree of acetalization is 30-40%. Vinylon, which is a water-insoluble material, should preferably have a wettability of about 62 N/m and a hygroscopicity of no less than 2%. By making at least part of the cover using such Vinylon, both of the dehumidification region and the high-wettability region can be provided by the Vinylon. For example, when a surface of the cover which becomes an inner surface of the capillary is made of Vinylon, the inner surface of the capillary (the inner surface of the cover) provides the high-wettability region and the dehumidification region throughout the length. With this structure, the speed of travel of the sample liquid along the inner surface of the cover can be reliably increased, whereby variations in the travel speed can be reduced. Further, the influences of moisture can be reliably reduced.

To ensure such effects, it is preferable to use a cover entirely made of Vinylon or a cover including a base at least one surface of which is covered with a Vinylon layer. Since such a cover has end portions made of Vinylon, a dehumidification region can be provided adjacent to the first and the second openings. When the cover is entirely made of Vinylon or opposite surfaces of the base of the cover are provided with Vinylon layers, it is possible to positively remove water existing around the capillary as well as water entering the capillary through the first and the second openings.

The wettability of Vinylon after it is heated at 80-140° C. for one second is no less than 57 mN/m. Therefore, even when the cover is fixed to the substrate using a hot-melt adhesive which melts at a temperature no more than 140° C., the high wettability of the inner surface of the capillary can be maintained. Therefore, it is possible to dispense with a hydrophobic double-sided tape, which causes the sample liquid to flow faster near the spacers than at other portions. Thus, it is possible to reduce variations in the liquid travel speed in the capillary while enhancing the measurement accuracy and the reproducibility.

For example, the capillary may have a uniform rectangular cross section. In that case, the cross section has a height H of 30-100 μm and a width W of 0.5-1.5 mm while satisfying W/H<18.

The analyzing instrument of the present invention may further comprise a liquid pooling portion communicating with the capillary and having a portion wider than the capillary. For example, the capillary is formed by laminating a cover on a substrate. In that case, the liquid pooling portion opens through a hole formed on the substrate or the cover and penetrating thicknesswise.

Preferably, at least a surface of the substrate or the cover defining the liquid pooling portion has a wettability of no less than 57 mN/m. For this purpose, at least part of the substrate or the cover is made of Vinylon, for example.

The analyzing instrument according to the present invention may include a spacer disposed between the substrate and the cover. In that case, the spacer includes mutually spaced portions defining a width of the capillary and the liquid pooling portion.

According to a second aspect of the present invention, there is provided an analyzing instrument comprising a substrate, a cover laminated on the substrate, a capillary for moving a sample liquid, and a liquid pooling portion communicating with the capillary and having a portion wider than the capillary.

Preferably, the liquid pooling portion opens through a hole formed on the substrate or the cover and penetrating thicknesswise.

Preferably, at least a surface of the substrate or the cover defining the liquid pooling portion has a wettability of no less than 57 mN/m.

The substrate or the cover may be made of Vinylon, for example.

The analyzing instrument according to the present invention may further comprise a spacer disposed between the substrate and the cover. In that case, the spacer includes mutually spaced portions defining a width of the capillary and the liquid pooling portion.

Preferably, the substrate or the cover may be provided with an adhesive layer arranged adjacent the cutout and having a higher adhesion than the substrate or the cover.

According to a third aspect of the present invention, there is provided an analyzing instrument comprising a substrate, a cover laminated on the substrate, and a capillary for moving a sample liquid, and at least part of the cover is made of Vinylon.

BRIEF DESCRIPTION OF THE DRAWINGS

FIG. 18A is a graph showing the reproducibility of the biosensor of the invention when Hct is 0%, whereas

FIG. 19A is a graph showing the reproducibility of the biosensor of the invention when Hct is 25%, whereas

FIG. 20A is a graph showing the reproducibility of the biosensor of the invention when Hct is 42%, whereas

FIG. 23 are a sectional view of a prior art biosensor and an enlarged view of the principal portion.

FIGS. 24 A and B are plan views for describing the manner of traveling of blood through the capillary in the prior art biosensor.

BEST MODE FOR CARRYING OUT THE INVENTION

Figure 1:
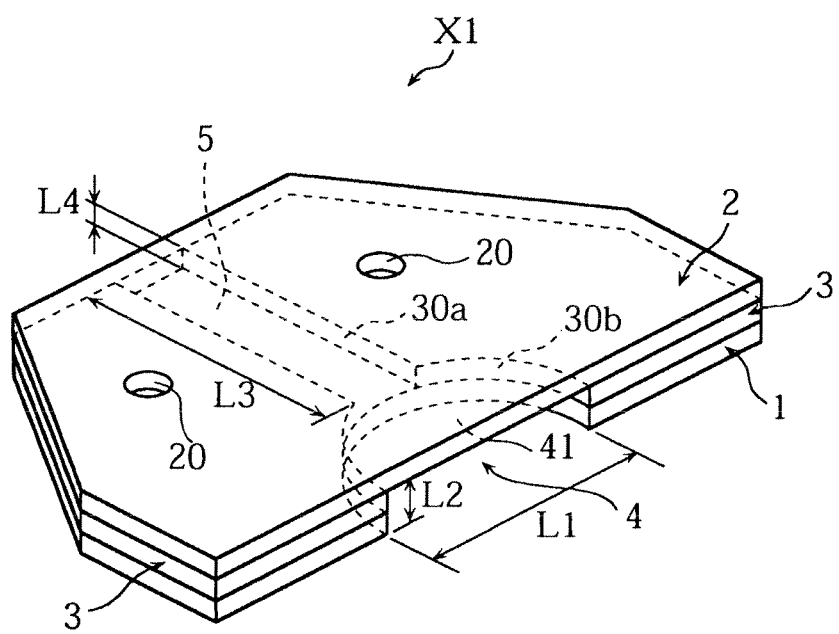
FIG. 1 is a perspective view illustrating a biosensor according to a first embodiment of the present invention.
Figure 2:
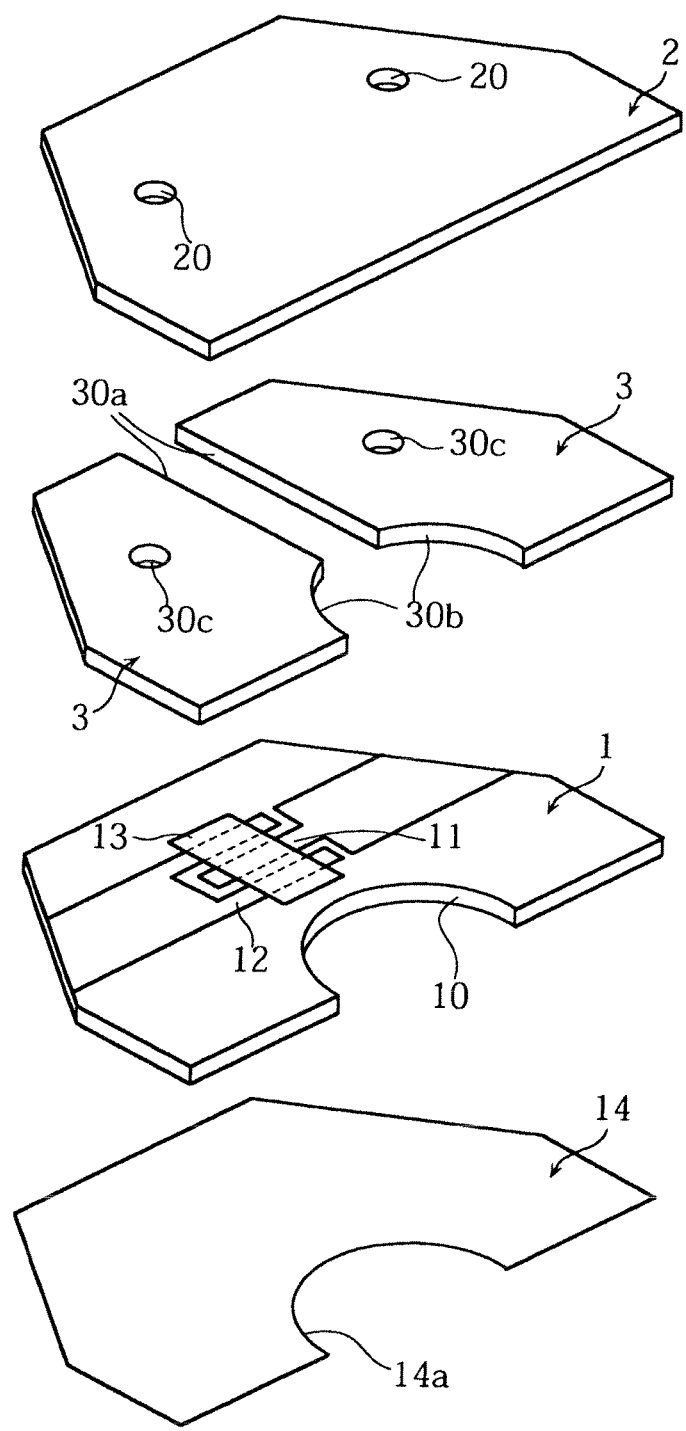
FIG. 2 is an exploded perspective view of the biosensor shown in FIG. 1.

A first embodiment of the present invention will be described with reference FIGS. 1 through 10. FIGS. 1 and 2 will be referred to for describing a biosensor according to the first embodiment, whereas FIGS. 3 through 10 will be referred to for describing applications and functions of the biosensor.

The biosensor X1 shown in FIGS. 1 and 2, which is mounted in use to a blood glucose level measuring apparatus, is a disposable unit. The biosensor X1 includes a substrate 1, a cover 2 and two spacers 3. The biosensor X1 is formed with a liquid pooling portion 4 and a capillary 5 which are defined by the substrate 1, the cover 2 and the two spacers 3.

The substrate 1 is made of an insulating material such as epoxy glass or PET and is formed with a semicircular cutout 10, as shown in FIG. 2. The cutout 10 defines an opening for the liquid pooling portion 4 on the side of the substrate 1.

The substrate 1 has an upper surface provided with an operative electrode 11, a counterpart electrode 12 and a reagent portion 13.

The operative electrode 11 includes a relatively narrow portion facing the capillary 5. The counterpart electrode 12 includes a forked portion flanking the narrow portion of the operative electrode 11. The reagent portion 13 is in a solid state and contains oxidoreductase and an electron carrier. The reagent portion 13 is arranged in the capillary 5 and kept in contact with the operative electrode 11 and the counterpart electrode 12. As oxidoreductase, use may be made of glucose oxidase which oxidizes glucose in blood to gluconic acid while reducing the electron carrier. As the electron carrier, use may be made of potassium ferricyanide.

The substrate 1 has a lower surface to which an adhesive sheet 14 is attached. The adhesive sheet is generally equal in dimension to the substrate 1 and is formed with a cutout 14a. The adhesive sheet 14 may comprise e.g. a gel sheet containing water gel and acrylic resin or a double-sided adhesive tape. Preferably, the adhesive sheet comprises a silicone gel sheet. As will be described later, in supplying blood to the biosensor X1, the skin is brought into contact with the lower surface of the substrate 1 via the adhesive sheet 14. Therefore, the adhesive sheet 14 bonded to the substrate 1 enhances the adhesion between the skin and the biosensor X1 in supplying blood to the biosensor X1.

The paired spacers 3 have the same configuration and are disposed symmetrically while being spaced from each other. Each of the spacers 3 includes a side surface 30a defining the capillary, and another side surface 30b connected thereto and defining the liquid pooling portion. The side surface 30b is curved along the cutout line of the substrate 1. Each spacer 3 is formed with a through-hole 30c penetrating thicknesswise. Each through-hole 30c is provided at a location corresponding to the operative electrode 11 or the counterpart electrode 12 of the substrate 1. The spacer 3 may comprise a double-sided tape or a hot-melt adhesive of a thermoplastic resin.

The cover 2 is fixed to the substrate 1 via the spacers 3. The cover 2 is formed with a pair of through-holes 20 penetrating thicknesswise. The through-holes 20 are provided at locations respectively corresponding to the operative electrode 11 and the counterpart electrode 12 of the substrate 1 and positionally correspond to the paired through-holes 30c formed in the spacers 3. When the biosensor X1 is mounted to a blood glucose level measuring apparatus, a pair of connectors of the blood glucose level measuring apparatus are inserted into the paired recesses defined by the through-holes 20 and the through-holes 30c, whereby the biosensor X1 is electrically connected to the blood glucose level measuring apparatus.

The cover 2 is entirely made of Vinylon, for example. Vinylon is a water-insoluble material having a hygroscopicity of no less than 2% and a wettability of about 62 mN/m. Therefore, the use of the cover 2 makes the inner surface of the capillary 5 (cover 2) a dehumidification region with a hygroscopicity of no less than 2% and also a water-insoluble high-wettability region having a wettability of no less than 57 mN/m.

However, the dehumidification region and the high-wettability region may be provided without making the cover 2 using Vinylon.

The liquid pooling portion 4 is defined by the cutout 10 of the substrate 1, the lower surface of the cover 2, and the side surfaces 30b of the paired spacers 3. The portion of the cover 2, which faces the liquid pooling portion 4, serves as a stage 41 for applying blood. The liquid pooling portion 4 has an outwardly open configuration defined by the cutout 10 formed in the substrate 1 and the side surfaces 30b of the spacer 3 which are curved along the cutout 10a. The liquid pooling portion 4 communicates with the capillary 5 and gradually increases in width as it extends away from the capillary 5. In this embodiment, the liquid pooling portion 4 has a maximum width L1 of 3-5 mm, a thickness L2 of 0.1-0.2 mm and a capacity of 1-6 µL.

The capillary 5 is defined by the upper surface of the substrate 1, the lower surface of the cover 2 and the side surfaces 30a of the paired spacers 3. The capillary 5 has one end communicating with the outside through the liquid pooling portion 4 and the other end also communicating with the outside. Thus, when blood is supplied through the liquid pooling portion 4, the blood travels through the capillary toward the other open end by capillary action. In this embodiment, the capillary 5 has a length L3 of 5.5-6.5 mm, a thickness L4 of 50-200 µm and a capacity of 0.3-5 µL.

Figure 3:
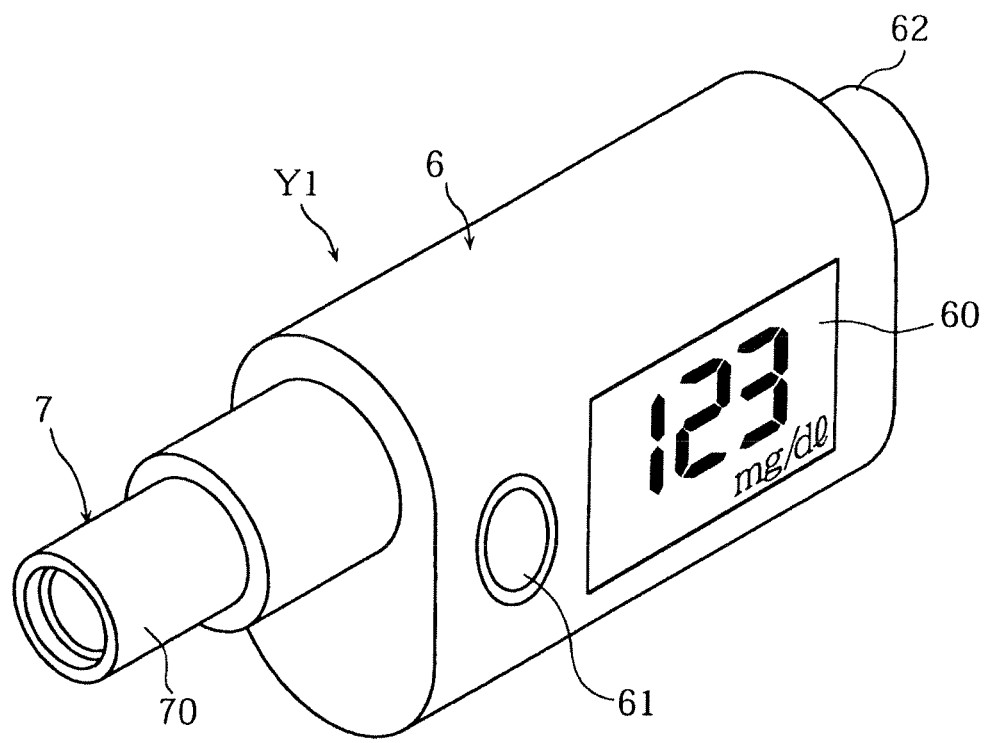
FIG. 3 is a perspective view illustrating a blood glucose level measuring apparatus which can utilize the biosensor according to the present invention.
Figure 4:
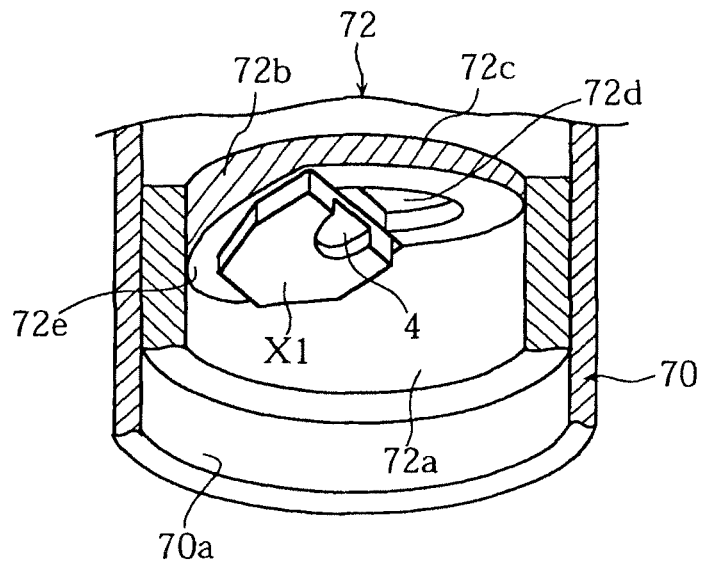
FIG. 4 is a perspective view, which is partially cut away, of a principal portion of the blood glucose level measuring apparatus shown in FIG. 3.

FIG. 3 is a perspective view of a blood glucose level measuring apparatus which can utilize the biosensor according to the present invention. FIG. 4 is a perspective view, which is partially cut away, of a principal portion of the blood glucose level measuring apparatus shown in FIG. 3. FIGS. 5 through 9 are sectional views illustrating a principal portion of the blood glucose level measuring apparatus for describing the operation for introducing blood to the biosensor.

Figure 5:
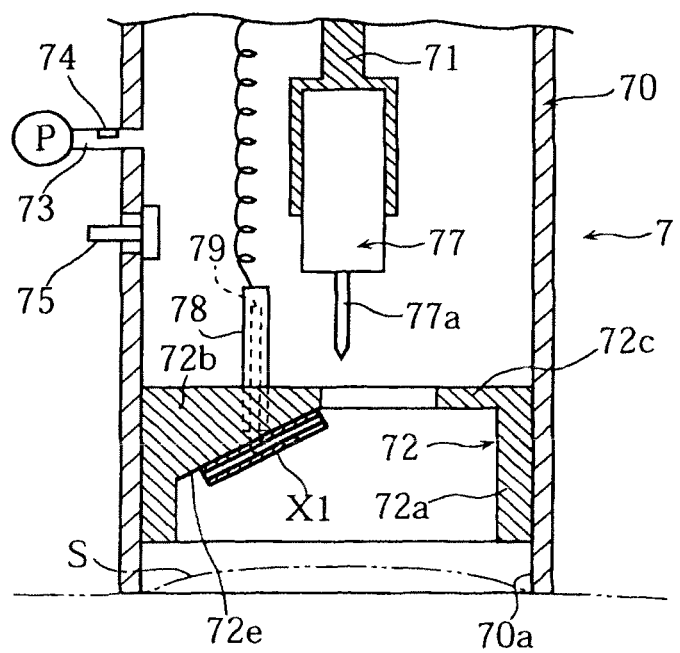
FIGS. 5-9 are sectional views illustrating a principal portion of the blood glucose level measuring apparatus for describing the operation for introducing blood to the biosensor.

As shown in FIG. 3, the blood glucose level measuring apparatus Y1 includes a main body 6, and a pressing unit 7 extending outward from the main body 6. The main body 6 is provided with a display 60 which may be e.g. a liquid crystal display or an LED display, an operation switch 61 which is operated in starting a series of process steps for measuring blood glucose level, and a press switch 62 for operating the lancet. As shown in FIGS. 4 and 5, the pressing unit 7 includes a cylindrical member 70, a lancet holder 71 reciprocally movable within the cylindrical member 70, and a sensor holder 72 fixed adjacent to an opening 70a of the cylindrical member 70.

A pump P is connected to the cylindrical member 70 via a connection pipe 73 communicating with the inside of the cylindrical member. The pump P can evacuate air from the inside of the cylindrical member 70 to depressurize the inside of the cylindrical member 70. The pump P may be incorporated in the main body 6 or may be provided outside as a separate portable member. The connection pipe 73 is provided with a pressure sensor 74 for measuring the pressure in the cylindrical member 70.

The cylindrical member 70 is provided with a relief valve 75 as air intake means. The relief valve 75 is utilized for sucking air from the outside to return the pressure in the cylindrical member 70 to the atmospheric pressure. The relief valve 75 may be a solenoid valve, for example. The relief valve 75 may be opened manually.

The lancet holder 71 detachably holds a lancet 77 having a lancing needle 77a made of e.g. metal. The lancet holder 71 is connected to a reciprocal driving mechanism not shown in the figure. Thus, when the press switch 62 (See FIG. 3) of the main body 6 is pressed, the lancet holder instantaneously moves reciprocally axially of the pressing unit 7 by the electromagnetic effect or the resilient force of a spring. As a result, the lancet 77 instantaneously moves toward the opening 70a of the cylindrical member 70 and then retreats away from the opening 70a.

The sensor holder 72 includes a cylindrical portion 72a, a sensor mount portion 72b formed inwardly of the cylindrical portion 72a, an arch portion 72c, and a window 72d surrounded by the sensor mount portion 72b and the arch portion 72c. The sensor mount portion 72b includes an inclined surface 72e on the side closer to the opening 70a of the cylindrical member 70. The biosensor X1 is attached to the inclined surface 72e. The window 72d allows the lancing needle 77a of the lancet 77 to pass therethrough when the lancet 77 moves reciprocally axially of the cylindrical member 70.

The sensor holder 72 is provided with a pair of connectors 78 penetrating through the sensor mount portion 72b. It is to be noted that FIGS. 4 and 5 show only one connector 78 on the front side. Each of the connectors 78 holds a connector pin 79, allowing the front end of the pin to project under resilience. When the biosensor X1 is mounted to the sensor mount portion 72b, the front end of each connector pin 79 projecting from the connector 78 is brought into contact with the operative electrode 11 or the counterpart electrode 12 of the biosensor X1.

The measurement of the blood glucose level using the above blood glucose level measuring apparatus is performed as follows. First, with the biosensor X1 mounted to the blood glucose level measuring apparatus Y1, the front end of the pressing unit 7 of the measuring apparatus is pressed against the skin S of an arm or a finger of the user, as shown in FIG. 5. At that time, the pressing unit 7 is temporarily closed hermetically by the cylindrical member 70 and the surface of the skin S.

Figure 6:
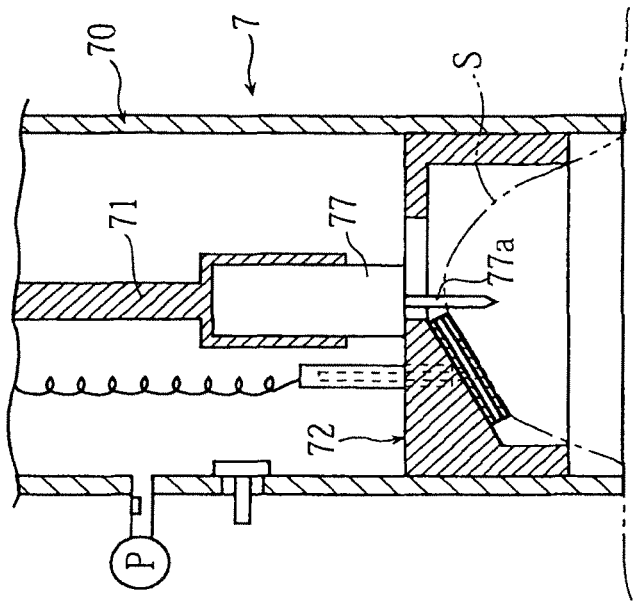

Subsequently, the operation switch 61 of the main body 6 (See FIG. 3) is pressed to drive the pump P. By this operation, the internal pressure of the pressing unit 7 or the cylindrical member 70 reduces gradually. As a result, the skin S closing the front end of the pressing unit 7 gradually bulges in accordance with the pressure drop to eventually come into contact with the biosensor X1 mounted to the sensor holder 72, as shown in FIG. 6. At that time, since the adhesive sheet 14 is attached to the substrate 1 of the biosensor X1, the biosensor X1 closely fits to the skin S. The close fitting of the biosensor X1 to the skin S prevents blood from entering between the biosensor X1 and the skin S in supplying blood, as will be described later.

When the pressure sensor 74 detects a predetermined pressure at which the skin S bulges sufficiently for close contact with the biosensor X1, the driving of the pump P is stopped, thereby finishing the depressurization. At that time, the finishing of the depressurization may be indicated on the display 60 (See FIG. 3).

Figure 7:
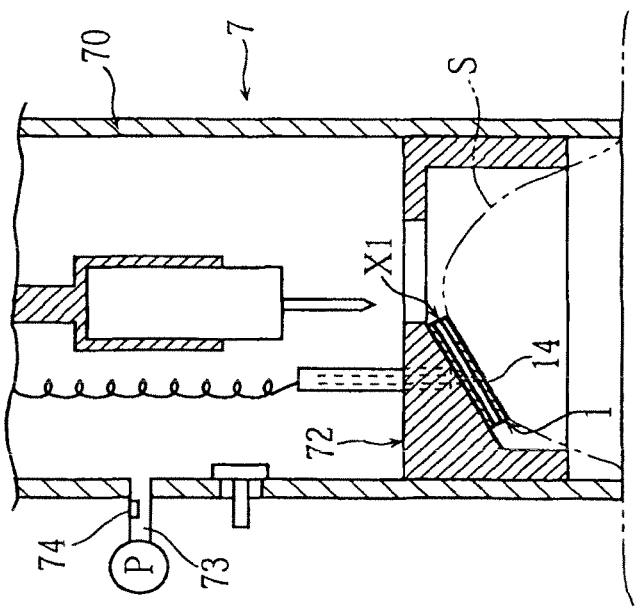

Subsequently, after confirming the finish of the depressurization, the user presses the press switch 62 (See FIG. 3) to instantaneously move the lancet holder 71 reciprocally. By this operation, the lancing needle 77a of the lancet 77 passes through the window 72d of the sensor holder 72 to lance the skin S, as shown in FIG. 7. At that time, the sensor holder 72 engages the lancet 77 to restrain the movement of the lancet 77. Specifically, when the lancing needle 77a enters the skin S to an appropriate depth, the lancet holder 77 engages the lancet 72 to prevent the lancing needle 77a from further entering the skin S. Thus, excessive lancing of the skin S by the lancing needle 77a is prevented.

Figure 8:
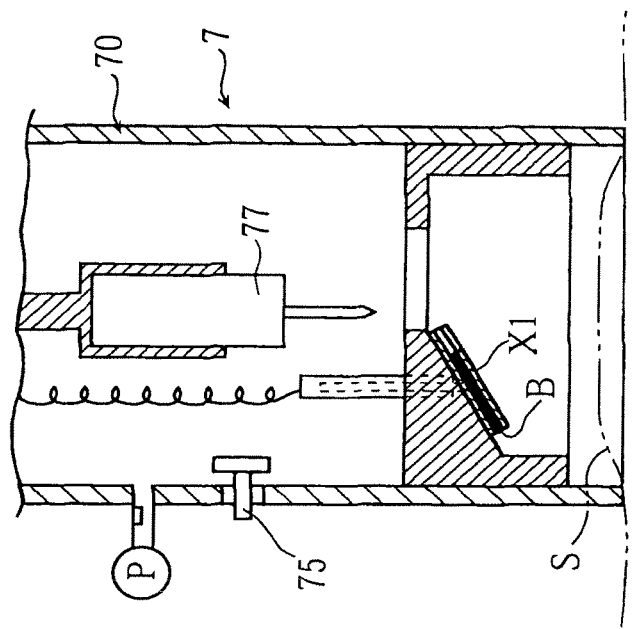

After the lancet 77 is then retreated as shown in FIG. 8, blood B bleeds from the skin S lanced by the lancing needle 77a. The biosensor X1 is so mounted to the sensor holder 72 that the liquid pooling portion 4 is located close to the lanced portion of the skin S. Therefore, the blood B is readily received in the liquid pooling portion 4 of the biosensor X1.

FIGS. 10A through 10D schematically illustrate the manner for supplying the blood B to the biosensor X1. In FIGS. 10A through 10D, the illustration of the substrate 1 of the biosensor X1 is omitted.

Figure 10A:
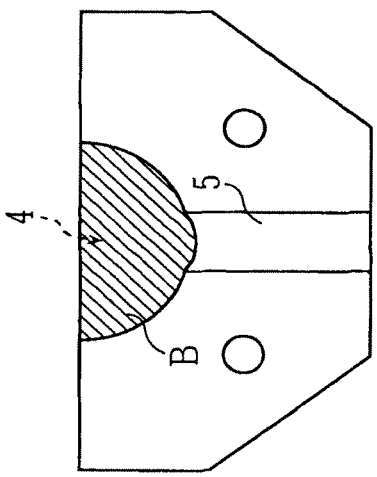
FIGS. 10 A-D are schematic diagrams illustrating the introduction of blood from the liquid pooling portion to the capillary.

As shown in FIG. 10A, the blood B extracted in the process step shown in FIG. 8 contacts the stage 41 of the liquid pooling portion 4. At that time, even when the bleeding portion is offset from the widthwise center of the liquid pooling portion 4, the blood B can be properly received in the liquid pooling portion because the liquid pooling portion 4 is widely open. Since the surface of the stage 41 has a high wettability, the blood B reaching the stage 41 spreads over the stage 41 with good wetting and on the inner surfaces of the liquid pooling portion 4. In this way, the blood of an amount sufficient for the blood glucose level measurement is supplied to the liquid pooling portion 4 while, at the same time, the blood is prevented from traveling through a localized area in the liquid pooling portion 4 before reaching the entrance of the capillary.

Figure 10C:
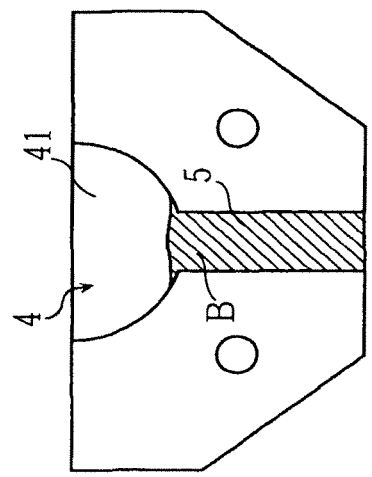
Figure 10B:
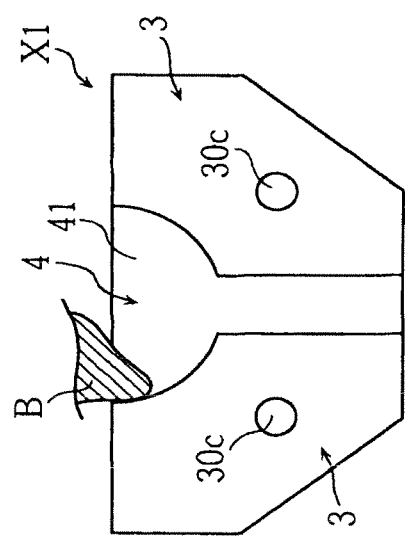
Figure 10D:
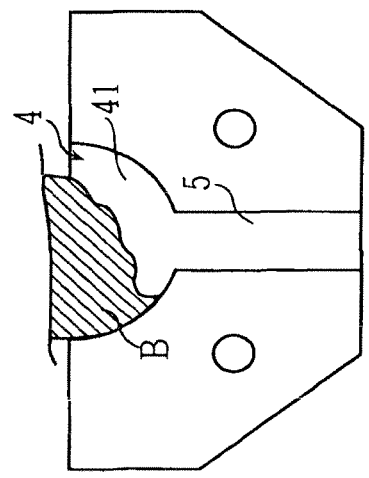

When the blood B closes the entrance of the capillary 5 as shown in FIG. 10C, the blood B is immediately guided into the capillary 5 by capillary action, as shown in FIG. 10D.

With the biosensor X1, blood B is supplied through the widely open liquid pooling portion 4. Therefore, automatic blood supply can be realized even with the lancet-integrated blood glucose level measuring apparatus Y1 which hinders visual confirmation. Since the traveling of the blood B to the capillary 5 starts when the blood B closes the entrance of the capillary 5, blood B can be supplied to the liquid pooling portion 4 even during the bleeding process before the amount necessary for the measurement is reached.

The blood B guided into the capillary 5 immediately dissolves the reagent portion 13 (See FIG. 2) provided on the substrate 1 to form a liquid phase reaction system. As a result, glucose contained in the blood is oxidized by the action of oxidoreductase contained in the reagent portion 13 (See FIG. 2). The electrons removed from glucose by this reaction is transferred to the electron carrier via enzyme. Specifically, the electron carrier is reduced by enzyme. Thereafter, when a voltage is applied across the operative electrode 11 and the counterpart electrode 12 via the paired connectors 78, the electrons are supplied from the liquid phase reaction system to the operative electrode 11 (See FIGS. 2 and 9). In the blood glucose level measuring apparatus Y1, the amount of the electrons supplied via the operative electrode 11 is measured as oxidation current, based on which the blood glucose level is calculated.

Figure 9:
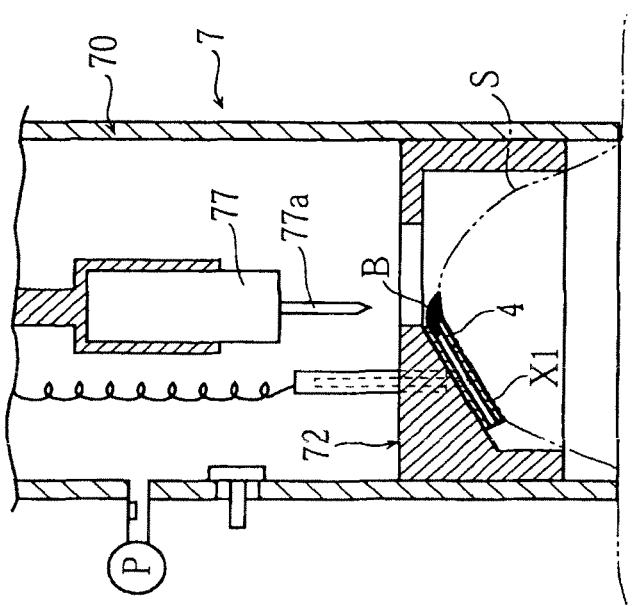

After the supply of the blood B to the biosensor X1 is completed, the interior of the cylindrical member 70 is exposed to the atmosphere by operating the relief valve 75, as shown in FIG. 9. As a result, the internal pressure of the cylindrical member 70 returns to the atmospheric pressure so that the skin S returns to its initial shape. The exposure to the atmosphere by the relief valve 75 may be performed manually by the user or automatically in the blood glucose level measuring apparatus Y1 after the supply of blood to the biosensor X1 is detected by the apparatus Y1.

Although a biosensor which is mounted, in use, to a blood glucose level measuring apparatus is exemplarily described in the above embodiment, the present invention is not limited thereto. For example, the structure of the above embodiment may be used for measuring cholesterol or lactic acid instead of glucose concentration. Although the cutout 10 for defining the liquid pooling portion 4 is formed in the substrate 1 in the above embodiment, such a cutout may be formed in the cover 2 instead. In performing the blood glucose level measurement using the biosensor having such a structure, the biosensor X1 need be mounted to the sensor holder 72 of the blood glucose level measuring apparatus Y1 with the cover 2 facing the opening 70a for coming into close contact with the skin S.

Next, a second embodiment of the present invention will be described with reference to FIGS. 11 through 14.

Figure 11:
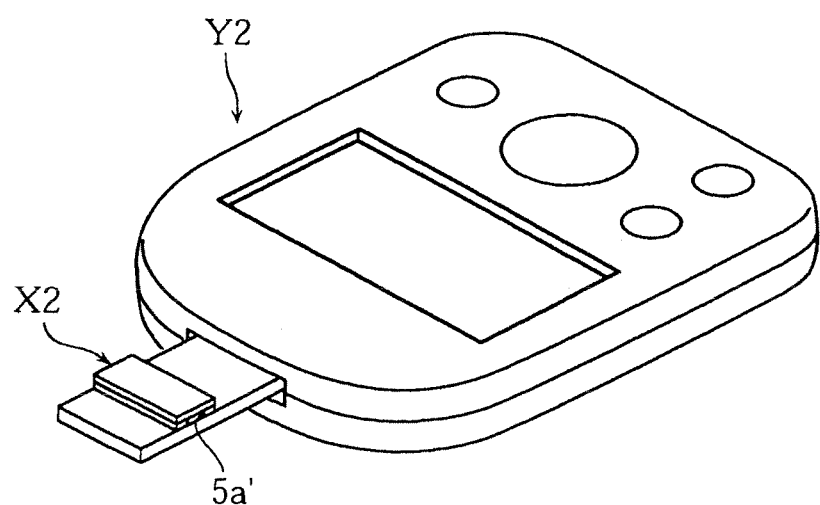
FIG. 11 is a perspective view illustrating a biosensor according to a second embodiment of the present invention mounted to a blood glucose level measuring apparatus.

As shown in FIG. 11, the biosensor X2 is of a simplified version and in use mounted to a blood glucose level measuring apparatus Y2 which is separate from a lancet.

Figure 12:
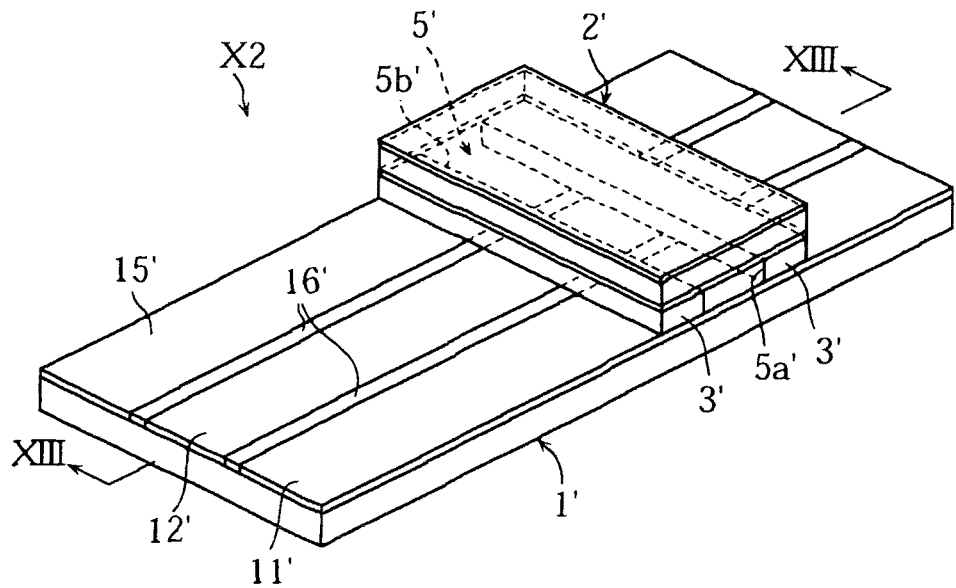
FIG. 12 is an entire perspective view of the biosensor shown in FIG. 11.
Figure 13:
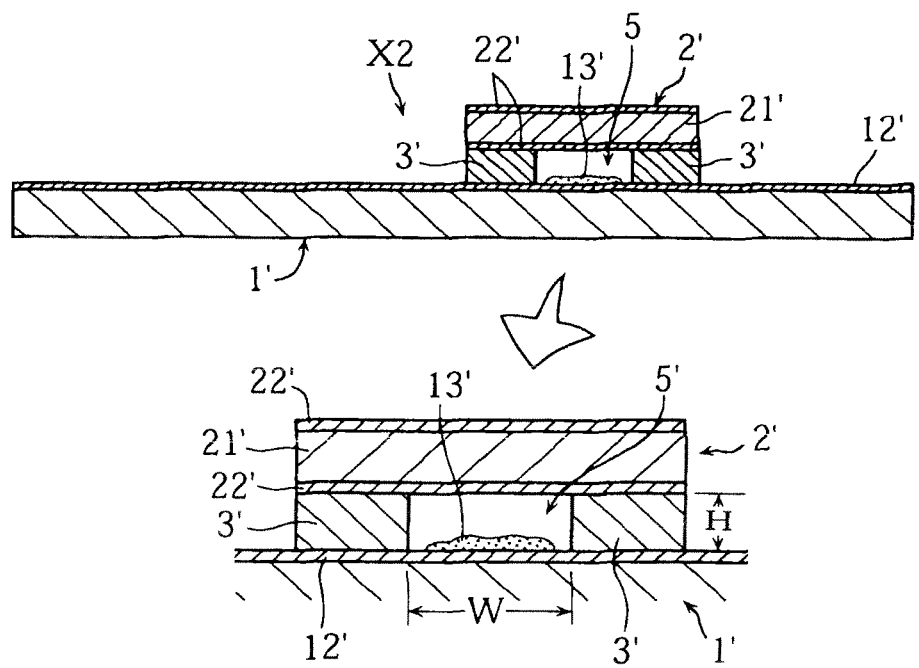
FIG. 13 are a sectional view taken along lines XIII-XIII in FIG. 12 and an enlarged view of a principal portion.
Figure 14:
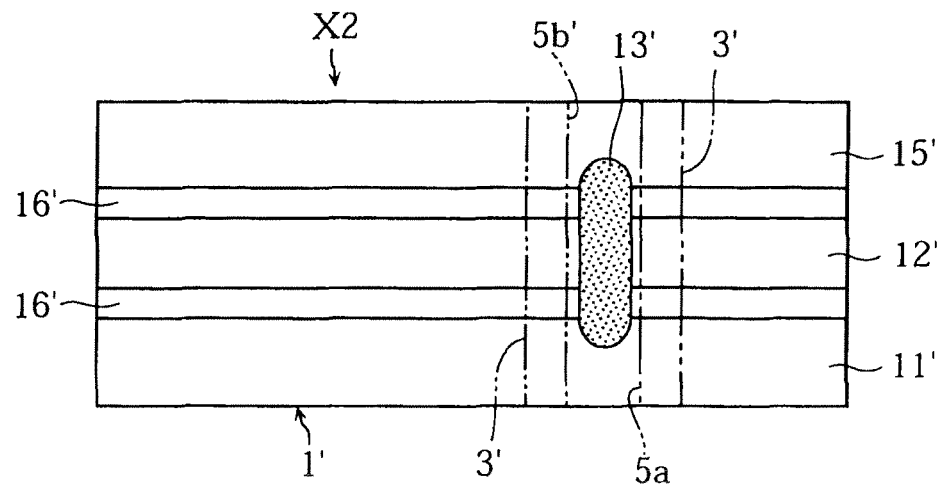
FIG. 14 is a plan view of the biosensor shown in FIG. 12 in a state without the cover and the spacers.

As shown in FIGS. 12 through 14, the biosensor X2 includes a rectangular substrate 1', and a cover 2' laminated on the substrate via spacers 3'. The biosensor X2 includes a capillary 5' defined by the substrate 1', the cover 2' and the spacers 3' and extending widthwise of the substrate V. Unlike the biosensor X1 shown in FIGS. 1 and 2, the biosensor X2 is not provided with a liquid pooling portion 4.

The substrate 1' has an upper surface provided with three electrodes, i.e. an operative electrode 11', a counterpart electrode 12' and a reference electrode 15'. The three electrodes 11', 12' and 15' are in the form of a strip extending longitudinally of the substrate V. Between adjacent ones of the electrodes 11', 12' and 15' is provided an insulating layer 16'.

A reagent layer 13' in a solid state is formed on the electrodes 11', 12' and 15'. The reagent layer 13' extends widthwise of the substrate 1' to continuously cover the electrodes 11', 12' and 15'.

The two spacers 3' are provided on opposite sides of the reagent layer 13' and extend widthwise of the substrate 1' to sandwich the reagent layer 13'. The spacers 3' may comprise a double-sided tape or a hot-melt adhesive of a thermoplastic resin.

The cover 2' comprises a base 21' and Vinylon sheets 22' laminated thereon. The base 21' may have a thickness of e.g. 100-150 μm, whereas each of the Vinylon sheets 22' has a thickness of e.g. 15-20 μm.

By the use of the cover 2' having such a structure, the inner surface of the capillary 5' (cover 2') becomes a dehumidification region with a hygroscopicity of no less than 2% and also a water-insoluble high-wettability region having a wettability of no less than 57 mN/m. Since end surfaces of the Vinylon sheet 22' of the cover 2' are exposed, opposite ends of the capillary 5 (portions adjacent openings 5a' and 5b') also serve as a dehumidification region.

Figure 15:
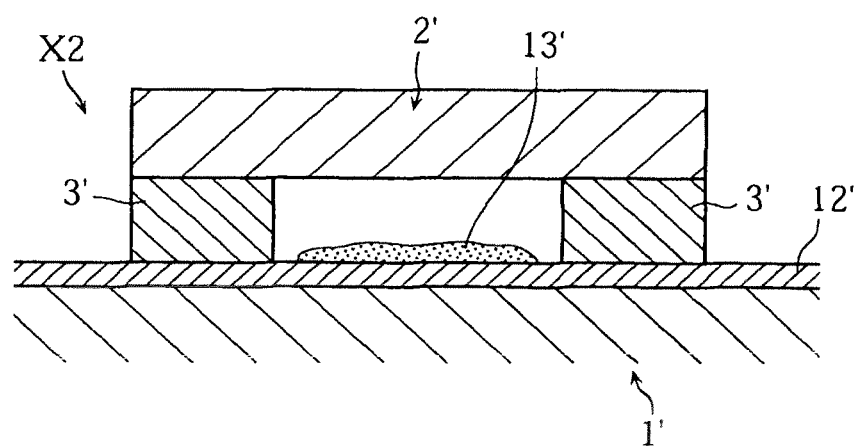
FIG. 15 is an enlarged sectional view of a principal portion of the biosensor for describing another example of cover.

As shown in FIG. 15, the cover 2' may be entirely made of Vinylon. In such a case again, the entire inner surface of the cover 2' becomes a dehumidification region and a high-wettability region. Alternatively, only part of the inner surface of the cover 2', i.e. an end or a center portion of the cover 2', for example, may be made of Vinylon. In such a case again, a dehumidification region can be provided by Vinylon.

The inside of the capillary 5' communicates with the outside through the openings 5a' and 5b'. The capillary 5' has a uniform rectangular cross section whose height H and width W are determined by the thickness of the spacers 3 and the distance between the spacers, respectively. In the present invention, it is preferable that the height H be 30-100 μm, the width W be 0.5-1.5 mm and W/H<18, as will be described later.

In use, the biosensor X2 is mounted to the blood glucose level measuring apparatus Y2 as shown in FIG. 11, and blood is introduced through the opening 5a'. The blood introduced through the opening 5a' travels within the capillary 5' by capillary action. Since the cover 2' of the biosensor X2 is a water-insoluble high-wettability region, even the blood having a high viscosity readily moves along the cover 2'. Since the high-wettability region is water-insoluble, the traveling of the blood does not cause a change in the wettability on the inner surface of the cover 2' and hence does not disadvantageously affects the travel speed of blood.

Since the inner surface of the cover 2' is made of Vinylon which is water-insoluble, it is not necessary to apply a surface-active agent on the surface of the cover 2' to enhance the hydrophilicity. Therefore, unlike the prior art structure, it is possible to prevent the ingress of a surface-active agent in the sample liquid and its movement together with the sample liquid. Regardless of whether the spacers 3' are made of a hydrophobic material or not, it is possible to avoid the situation in which the sample liquid flows much faster near the spacers 3' than at other portions, thereby reducing variations in the speed of the sample liquid. In this way, since the sample liquid can travel relatively fast with little variation in the speed, the sample liquid can reliably fill the capillary 5' quickly while reliably dissolving the reagent layer 13' quickly. Therefore, the blood glucose level can be measured accurately, and the measurement reproducibility is enhanced.

Figure 16:
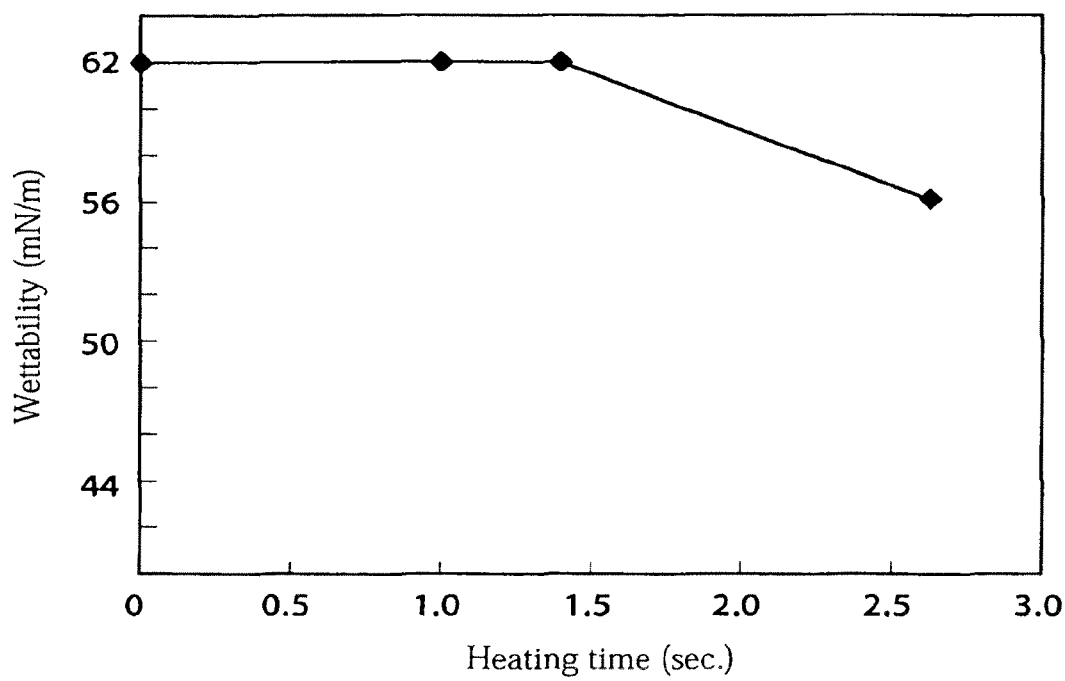
FIG. 16 is a graph showing the change of wettability relative to heating time of Vinylon.

As shown in FIG. 16, the inventors have confirmed that the wettability of Vinylon hardly changes even after it is heated at 140° C. for one second. Therefore, the cover 2' may be fixed to the substrate 1' using a hot-melt adhesive which melts at a temperature of no more than 140° C. In that case, the spacers 3' need not be made of a hydrophobic double-sided tape. It is therefore possible to avoid the situation wherein the sample liquid flows much faster on the spacers 3' than on the inner surface of the cover 2', thereby reducing variations in the speed of the sample liquid. As a result, the blood glucose level can be measured accurately, and the measurement reproducibility is enhanced.

In the biosensor X2, portions adjacent the openings 5a', 5b' and the inner surface of the capillary 5' (cover 2') is the dehumidification region. Therefore, even when water in the gas phase tends to enter the capillary 5' or actually enters the capillary 5', it is removed at the dehumidification region. Since the outer surface of the cover 2' is also made of Vinylon, water around the capillary can also be removed. Therefore, exposure of the reagent 13' to water (resulting in reduction of the electron carrier) is prevented, thereby enhancing the storage stability. Further, background current due to water is decreased so that the concentration of a target component in the sample liquid can be measured accurately. Moreover, it is possible to reduce variations in the suction speed among different biosensors caused by variations in moisture adsorption. This also enhances the measurement accuracy.

The inventors of the present invention examined the influences of hygroscopicity of the reagent layer on the suction speed (Example 1), the measurement reproducibility (Example 2) and the optimum capillary size (Example 3).

EXAMPLE 1

In this example, the influences of hygroscopicity of the reagent layer on the suction speed were examined. The examination was performed using inventive biosensors which were similar in structure to the biosensor X2 shown in FIGS. 12 through 14, and comparative glucose sensors similar in structure to that shown in FIG. 23. The detailed structure of the biosensors is given in Table 1 below. As shown in Table 1, each of the inventive biosensors used for the examination had a Vinylon sheet attached to only one surface of a PET material, unlike the biosensor X2 shown in FIGS. 12 through 14. In each of the comparative biosensors, lecithin as a surface-active agent is applied to one surface of a PET material as a cover.

TABLE 1

(BIOSENSOR STRUCTURE)

| | | Capillary Size | | |
|---|---|---|---|---|
| | Cover Structure | Total Length | Height H | Width W |
| Inventive Biosensor | PET of 100 μm to one surface of which Vinylon sheet of 17 μm is attached | 6 mm | 120 μm | 1.2 mm |
| Comparative Biosensor | PET of 100 μm with one surface hydrophilically treated by applying lecithin | | | |

In this example, four inventive biosensors and four comparative biosensors were prepared. The four inventive biosensors and the four comparative biosensors were respectively exposed to moisture for 0 minutes, 30 minutes, 60 minutes and 180 minutes before measuring the blook suction time. The results are given in FIG. 17. The moisture exposure was performed at 30° C. at relative humidity of 80%. The suction time refers to the time needed for completely filling the capillary with blood.

Figure 17:
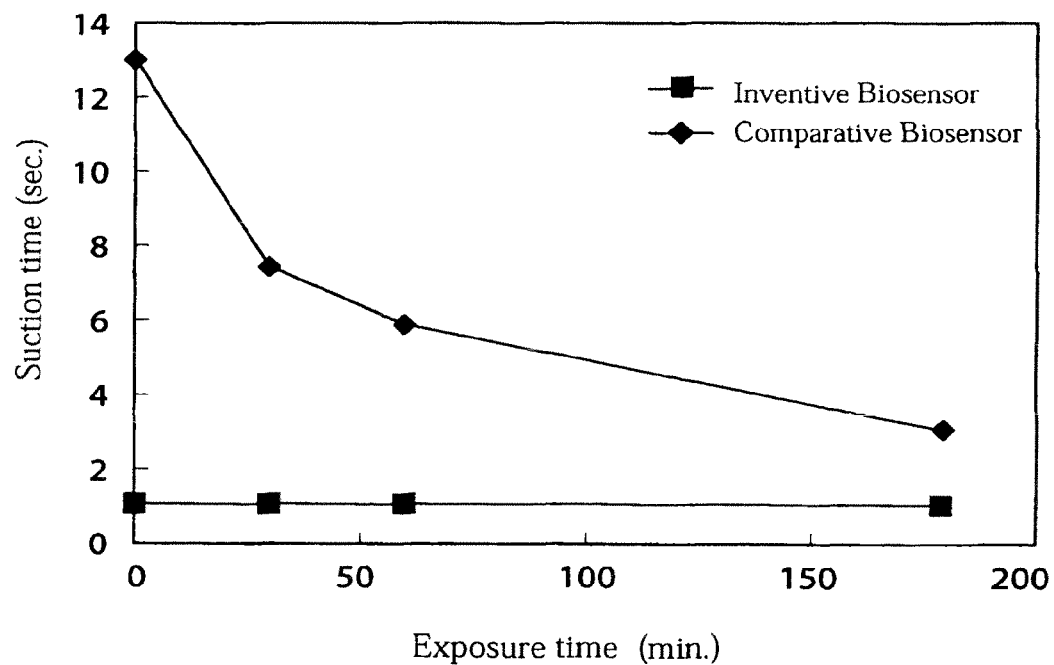
FIG. 17 is a graph showing the relationship between exposure time and suction time.

As shown in FIG. 17, the suction time of each inventive biosensor was generally constant regardless of the length of the exposure time. On the other hand, the suction time of each comparative biosensor became shorter as the exposure time was longer. From these results, it was observed that the comparative biosensor required a shorter suction time due to an increase of the exposure time which results in an increase of hygroscopicity to prompt dissolution of the reagent layer. On the other hand, each inventive biosensor restrained hygroscopicity by the reagent layer due to the dehumidification region provided by Vinylon, thereby keeping moisture dissolution of the reagent layer at a constant level. Therefore, it is concluded that the inventive biosensor has a good storage stability while providing a constant blood traveling speed in the capillary to reduce measurement deviations among different biosensors, thereby enhancing the measurement reproducibility.

EXAMPLE 2

Figure 18A:
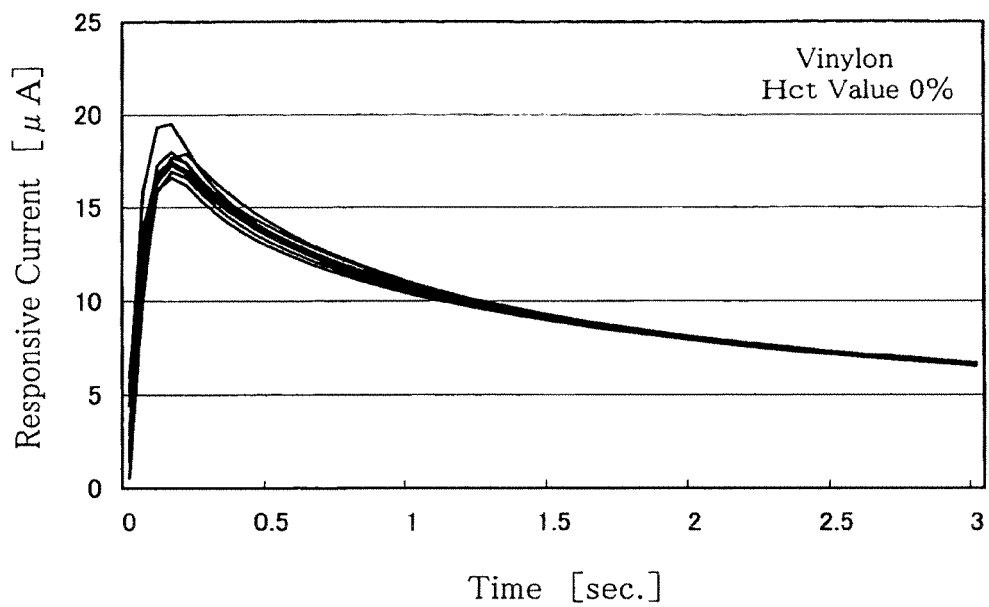
Figure 18B:
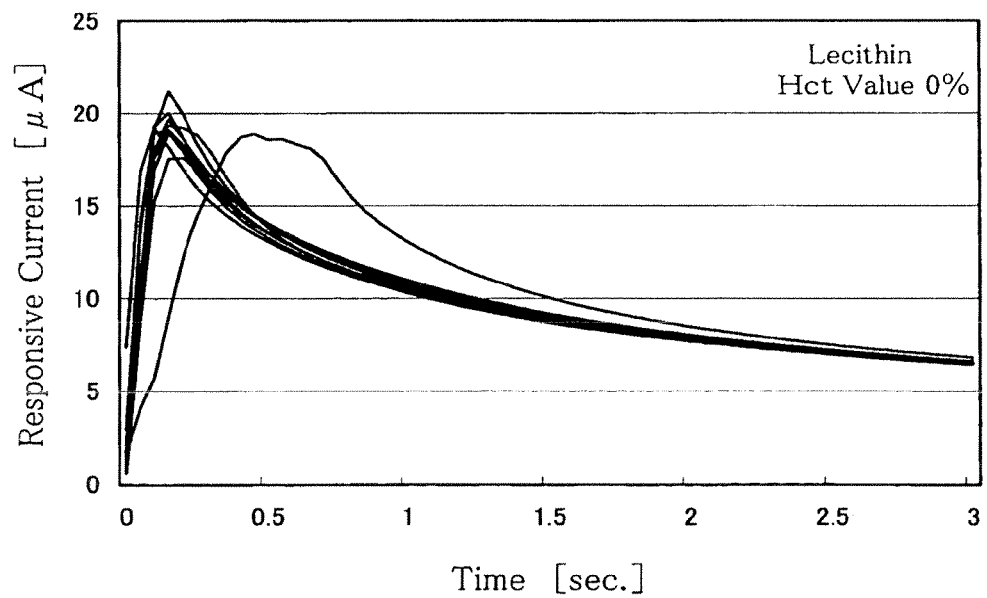
FIG. 18B is a graph showing the reproducibility of the comparative biosensor when Hct is 0%.
Figure 19A:
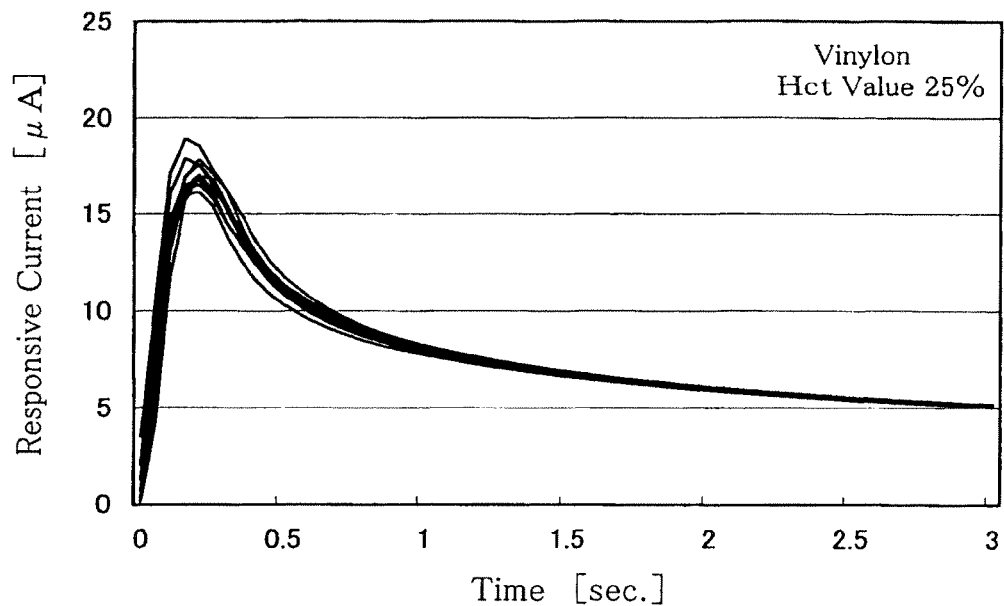
Figure 19B:
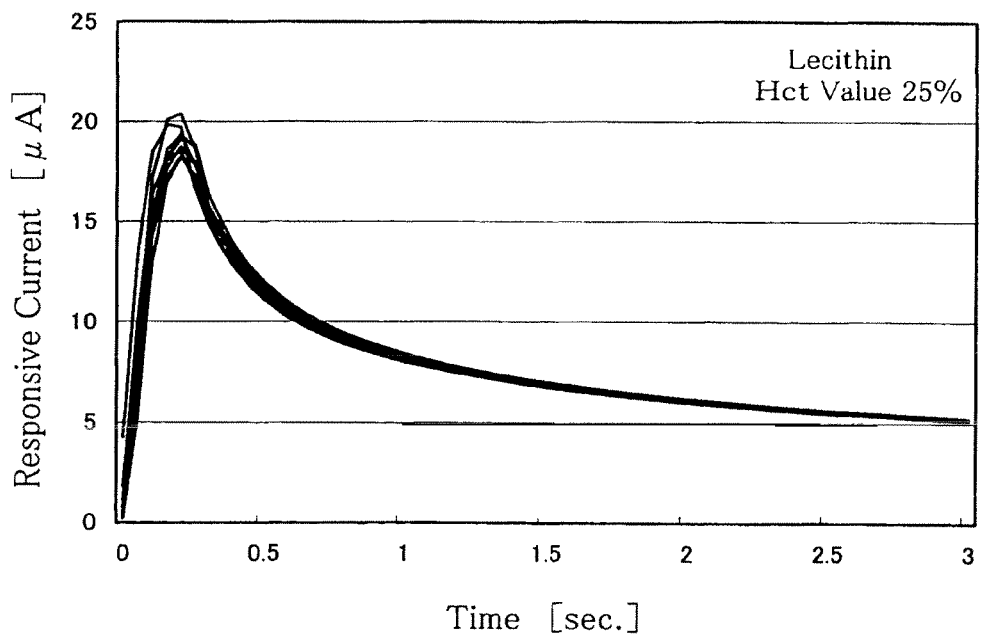
FIG. 19B is a graph showing the reproducibility of the comparative biosensor when Hct is 25%.
Figure 20A:
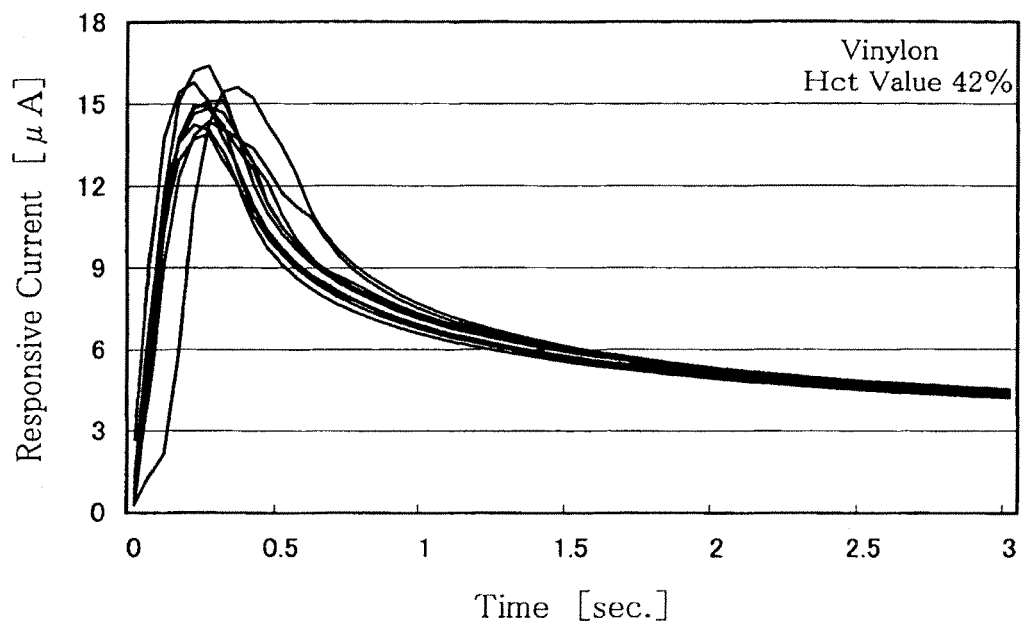
Figure 20B:
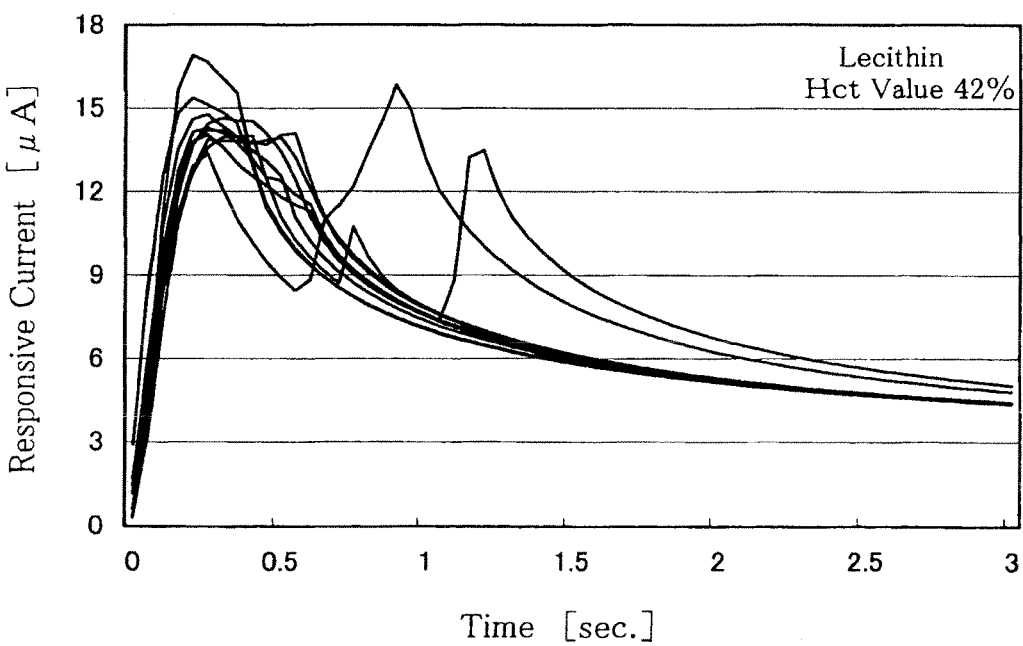
FIG. 20B is a graph showing the reproducibility of the comparative biosensor when Hct is 42%.

In this example, the measurement reproducibility was examined. The examination of the measurement reproducibility was performed by comparing inventive biosensors with comparative biosensors with respect to change of responsive current with time. Specifically, while a standard solution was supplied to the reagent layer, a constant voltage of 200 mV was applied across the operative electrode and the counterpart electrode. The value of oxidation current flowing in this state was measured as the responsive current. The standard solution was prepared by dissolving glucose in physiological saline to provide a glucose concentration of 100 mg/dL while adjusting the blood cell concentration (Hct) to an intended value. The results for the inventive biosensors are given in FIGS. 18A, 19A and 20A, whereas the results for the comparative biosensors are given in FIGS. 18B, 19B and 20B. FIG. 18, FIG. 19 and FIG. 20 show the results when the Hct was 0%, 25% and 42%, respectively. The responsive current was measured with respect to ten biosensor samples for each kind of biosensors at each Hct value.

As understood from the comparison between FIGS. 18A and 18B as well as between FIGS. 19A and 19B, when Hct was low (no more than 25%), the reproducibility hardly differed between the inventive biosensor of the invention and the comparative biosensor. However, as understood from the comparison between FIGS. 20A and 20B, when Hct is 42%, the reproducibility of the inventive biosensor is considerably better than that of the comparative biosensor within a time range of five seconds from the start of voltage application. To confirm this, the reproducibility of the responsive current for the ten inventive biosensor samples and the ten comparative biosensor samples when Hct was 42% is represented as relative standard deviation (C.V. [%]) in Table 2 below. Specifically, the reproducibility upon lapse of three seconds, four seconds and five seconds, respectively, from the start of voltage application is given in the Table.

TABLE 2

(EVALUATION OF REPRODUCIBILITY)

| Time of Sampling | Lapse of 3 seconds | | | Lapse of 4 seconds | | | Lapse of 5 seconds | | |
|---|---|---|---|---|---|---|---|---|---|
| Glucose Concentration [mg/dl] | 100 | 400 | 600 | 100 | 400 | 600 | 100 | 400 | 600 |
| Inventive Biosensor C.V. [%] | 2.46 | 1.67 | 1.50 | 2.27 | 1.48 | 1.18 | 2.12 | 1.53 | 0.97 |
| Comparative Biosensor C.V. [%] | 5.20 | 2.94 | 2.17 | 3.70 | 2.99 | 1.85 | 3.13 | 3.16 | 1.80 |

As is clear from Table 2, regardless of the glucose concentration, the inventive biosensor exhibited less measurement deviations and hence provided better reproducibility than the comparative biosensor upon lapse of three to five minutes from the start of voltage application. Thus, it is concluded that the provision of the high-wettability region of Vinylon in the inventive biosensor enhances the reproducibility upon lapse of a relatively short time from the start of voltage application. The high-wettability region can be said to be particularly effective for shortening the measurement time for the blood having a relatively high Hct value (sample liquid having a high viscosity).

EXAMPLE 3

In this example, the optimum capillary size was determined. The suction time was measured in the same manner as in Example 1 with respect to biosensors 1-12 including inventive and comparative biosensors which were the same in basic structure as those used in Example 1 but which had various capillary sizes. To evaluate the suction time for a sample liquid having a high viscosity, a standard solution of 70% Hct was used. The results are given in Table 3. In actual measurement using a biosensor, it is desirable to fill the capillary in 2.5 seconds to shorten the measurement time. Therefore, for purposes of evaluation in Table 3, the mark ☺ is applied to the biosensor whose suction time was no more than 2 seconds, the mark O to the biosensor whose suction time was 2-2.5 seconds, the mark to the biosensor whose suction time was 2.5-5 seconds, and the mark X to the biosensor whose suction time was no less than 5 seconds.

TABLE 3

(EVALUATION OF SUCTION SPEED)

| | | Capillary Size | | | | |
|---|---|---|---|---|---|---|
| | Cover Structure | Total Length | Height H | Width W | W/H | Evaluation |
| Biosensor 1 | PET of 100 μm | 6 mm | 60 μm | 0.75 mm | 12.5 | Δ |
| Biosensor 2 | having one | | | 1.00 mm | 16.7 | Δ |
| Biosensor 3 | surface to which | | | 1.20 mm | 20.0 | X |
| Biosensor 4 | Vinylon sheet of | | 90 μm | 0.75 mm | 8.3 | ☺ |
| Biosensor 5 | 17 μm is attached | | | 1.00 mm | 11.1 | ☺ |
| Biosensor 6 | | | | 1.20 mm | 13.3 | ☺ |
| Biosensor 7 | PET of 100 μm | | 60 μm | 0.75 mm | 12.5 | X |
| Biosensor 8 | having one | | | 1.00 mm | 16.7 | X |
| Biosensor 9 | surface which is | | | 1.20 mm | 20.0 | X |
| Biosensor 10 | hydrophilically | | 90 μm | 0.75 mm | 8.3 | O |
| Biosensor 11 | treated by | | | 1.00 mm | 11.1 | O |
| Biosensor 12 | applying lecithin | | | 1.20 mm | 13.3 | Δ |

As shown in Table 3, each of the biosensors 1-6, in which the capillary (cover) has an inner surface comprising a dehumidification region and a high-wettability region, exhibits a higher suction speed than the biosensor which has a capillary of the same size and in which lecithin is applied to the inner surface of PET as the cover. From the above table, it is found that a capillary having a height H of 30-100 μm and a width W of 0.5-1.5 mm while satisfying W/H<18 is suitable for a sample liquid having a high viscosity.

Figure 21:
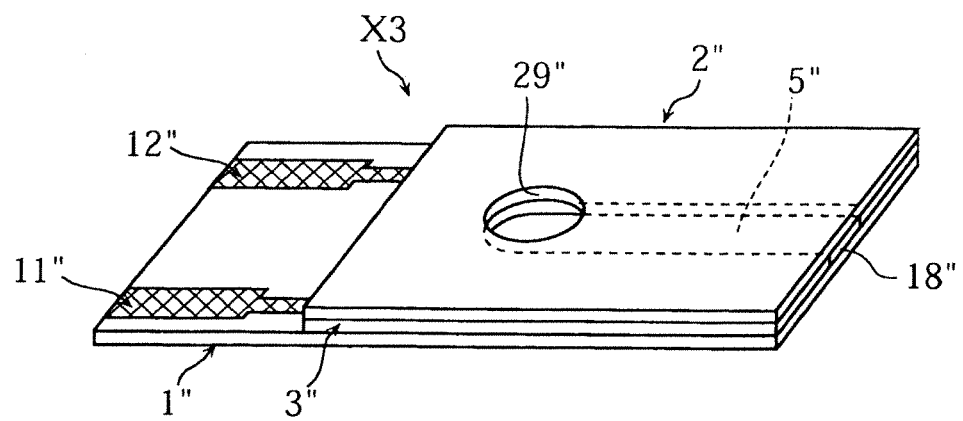
FIG. 21 is an entire perspective view illustrating a biosensor according to a third embodiment of the present invention.
Figure 22:
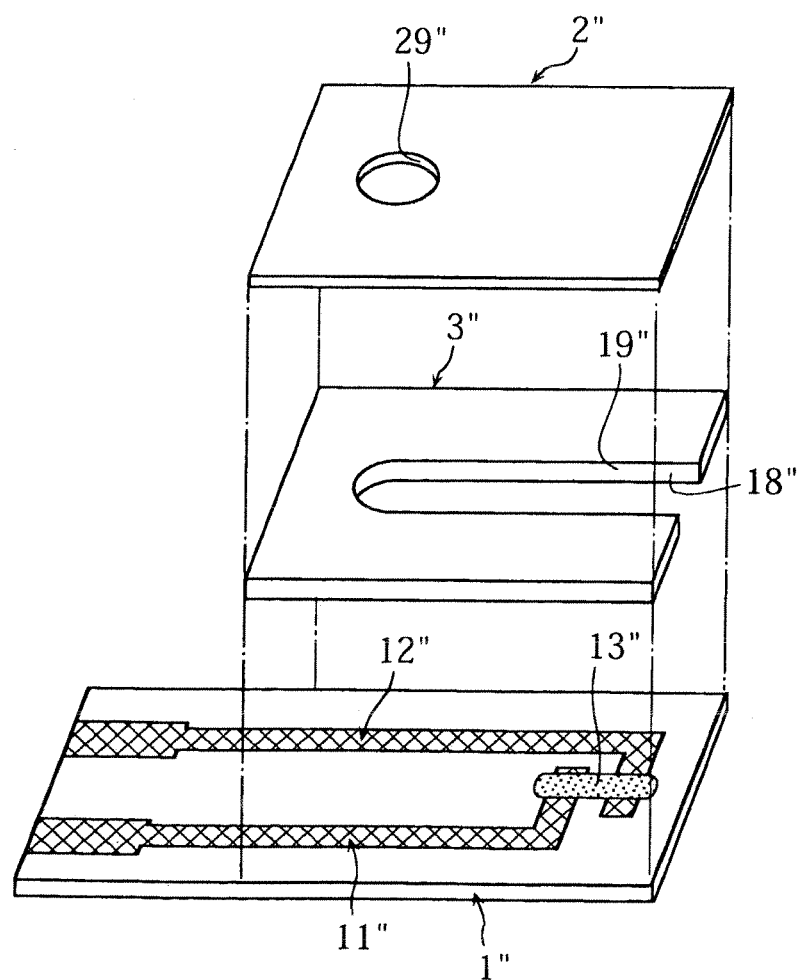
FIG. 22 is an exploded perspective view of the biosensor shown in FIG. 21.

The technical idea of the present invention is also applicable to a biosensor X3 according to a third embodiment, as shown in FIGS. 21 and 22. The biosensor X3 shown in these figures also includes a substrate 1", a spacer 3" and a cover 2" but differs from the biosensor X2 of the foregoing embodiment in configuration of the capillary 5' and structure of the electrodes 11" and 12".

Specifically, in the biosensor X3, the cover 2" is formed with a through-hole 29", whereas the spacer 3" is formed with a slit 19" extending longitudinally of the substrate 1" and having an open end 18". When the spacer 3" and the cover 2" are laminated on the substrate 4", the slit 19" communicates with the through-hole 29" to provide the capillary 5". The end 18" of the slit 19" serves as a sample introducing port. On the substrate 1" is provided an operative electrode 11" and a counterpart electrode 12". A reagent layer 13" is formed to continuously cover respective ends of the operative electrode 11" and the counterpart electrode 12".

In the biosensor X3 again, the cover 2" may be entirely made of Vinylon or may be prepared by attaching a Vinylon sheet to a base of e.g. PET so that the inner surface of the capillary 5" provides a dehumidification region and a high-wettability region. In the biosensor X3 again, only part of the inner surface of the capillary 5" provided by the cover 2" may be made to serve as a dehumidification region and a high-wettability region, or only selected portions adjacent the through-hole 29" and the sample introducing port 18" may be made to serve as a dehumidification region.

The biosensors X2, X3 of the second and the third embodiments may also be provided with a liquid pooling portion.

The invention claimed is:

1. A test instrument, comprising:
   a substrate;
   a plurality of electrodes on the substrate;
   a cover;
   one or more spacing members arranged between the substrate and the cover; and
   a sample chamber defined between the cover and the substrate at top and bottom, the one or more spacing members defining sidewalls of the sample chamber, the sample chamber extending inwardly from an opening at an edge of the test instrument, the sidewalls of the one or more spacing members extending continuously from the opening to the plurality of electrodes, the sample chamber having a first portion and a second portion, the first portion located adjacent the opening and defined by tapered and curved sidewalls, the cover and the substrate, the second portion located inward of the first portion, the second portion of the sample chamber having a reagent and a smaller width than the first portion, and a vent from the second portion to outside of the test instrument,
   wherein the reagent is between the opening of the test instrument and the vent such that a sample of blood is drawn by capillary action from the opening of the test instrument to the reagent portion.

2. The test instrument of claim 1, wherein the substrate is formed with a cutout defining the opening for the first portion of the sample chamber.

3. The test instrument of claim 1, wherein the cover is formed with a cutout defining the opening for the first portion of the sample chamber.

4. The test instrument of claim 1, wherein the sidewalls of the one or more spacing members are concave in the first portion of the sample chamber.

5. The test instrument of claim 1, wherein the sample chamber further comprises a cross-section that decreases in the first portion of the sample chamber and is substantially unchanged in the second portion of the sample chamber.

6. A test strip, comprising:
   a substrate including electrodes thereon;
   a cover;
   at least one spacing member arranged between the substrate and the cover and forming walls therebetween;
   a chamber defined between the cover, the substrate, and the walls of the at least one spacing member, the chamber having one or more receiving portions for transferring a sample of blood from a sample opening port at an outside edge of the test strip to the electrodes, the one or more receiving portions including at least a first component and a second component, the first component located adjacent the sample opening port and extending inward to the second component; and
   a vent from the second component to outside of the test strip,
   wherein the walls of the at least one spacing member define sides of the chamber and extend from the sample opening port to the electrodes, the sides of the first component being defined by tapered and curved walls of the at least one spacing member, the second component of the chamber having a reagent portion and a smaller cross-sectional area than the cross-sectional area of the first component of the chamber, the reagent portion is between the sample opening port of the test strip and the vent such that a sample of blood moves from the opening port of the test strip to the reagent portion by capillary action.

7. The test strip of claim 6, wherein the sides of the chamber are concave in the first component of the sample chamber.

8. The test strip of claim 6, wherein the chamber further comprises an angled transition portion at the intersection of the first and the second components of the sample receiving chamber.

9. The test strip of claim 6, wherein the sample opening port has an arched receiving portion.

10. A test strip for receiving a blood sample, comprising:
    a cover;
    a substrate;
    a plurality of electrodes;
    a spacing member located between the cover and the substrate;
    a sample chamber defined by inner surfaces of the cover, the substrate, and the spacing member;
    the sample chamber having an outer portion and an inner portion;
    an opening at an edge of the test strip formed by the cover, the substrate and the spacing member at the outer chamber portion, the spacing member having curved and tapered inner surfaces in the outer chamber portion and extending from about the opening at the outer chamber portion to the inner chamber portion where a reagent portion and the electrodes are located; and
    a vent from the inner chamber portion to outside of the test strip,
    wherein a width of the outer chamber portion at the opening being wider than a width of the inner chamber portion, and the reagent portion is between the opening of the test strip and the vent such that the blood sample is drawn by capillary action from the opening of the test strip to the reagent portion.

11. The test strip of claim 10, wherein the inner surfaces of the spacing member are concave in the outer chamber portion of the sample chamber.

12. The test strip of claim 10, wherein the sample chamber further comprises an angled transition portion at the intersection of the inner and outer portions of the sample chamber.

13. The test strip of claim 10, wherein the sample chamber further comprises a cross-section that decreases in the outer portion and is substantially unchanged in the inner portion.

14. The test strip of claim 10, wherein the sample chamber further comprises a cross-section that variably decreases in the outer portion and is substantially unchanged in the inner portion.

15. The test instrument of claim 1, wherein the sample chamber further comprises an angled transition portion at the intersection of the first and the second portions of the sample chamber.

16. The test strip of claim 6, wherein the substrate is formed with a cutout defining the opening for the first component of the chamber.

17. The test strip of claim 6, wherein the cover is formed with a cutout defining the opening for the first component of the chamber.

18. The test strip of claim 10, wherein the substrate is formed with a cutout defining the opening for the outer chamber portion of the sample chamber.

19. The test strip of claim 10, wherein the cover is formed with a cutout defining the opening for the outer chamber portion of the sample chamber.

20. The test instrument of claim 1, wherein the electrodes adjacent to the reagent are substantially parallel to the opening.

21. The test strip of claim 6, wherein the electrodes adjacent to the reagent portion are substantially parallel to the sample opening port.

22. The test strip of claim 10, wherein the electrodes adjacent to the reagent portion are substantially parallel to the opening.

23. The test instrument of claim 1, wherein the sidewalls of the first portion are continuously curved from the opening to the second portion.

24. The test strip of claim 6, wherein the sides of the first component are defined by continuously curved walls.

25. The test strip of claim 10, wherein the inner surfaces in the outer chamber portion are continuously curved from the opening to the inner chamber portion.

26. An analyzing instrument to measure a concentration of a sample liquid, comprising:
 a cover;
 a substrate;
 a plurality of electrodes on the substrate;
 a spacing member located between the cover and the substrate; and
 a sample liquid chamber defined by inner surfaces of the cover, the substrate, and the spacing member,
 a sample port of the sample liquid chamber defined at an outside edge of the analyzing instrument, the sample port at an outer portion of the sample liquid chamber having a width that is wider than a width at an inner portion of the sample liquid chamber, the sample liquid chamber having a curved, tapered portion in the outer portion, the spacing member extending from the sample port of the sample liquid chamber to the inner portion of the sample liquid chamber where a reagent and the electrodes are located, and a vent from the inner portion of the sample liquid chamber to outside of the analyzing instrument,
 wherein the reagent is located between the sample port and the vent such that the sample liquid is drawn by capillary action from the sample port to the reagent.

27. The analyzing instrument of claim 26, wherein the inner surfaces of the spacing member are concave in the outer portion of the sample liquid chamber.

28. The analyzing instrument of claim 26, wherein the sample liquid chamber further comprises a cross-section that decreases in the outer portion of the sample liquid chamber and is substantially unchanged in the inner portion of the sample liquid chamber.

29. The analyzing instrument of claim 26, wherein the sample liquid chamber further comprises an angled transition portion at the intersection of the outer and the inner portions of the sample liquid chamber.

30. The analyzing instrument of claim 26, wherein the inner surfaces of the spacing member in the outer portion are continuously curved from the sample port to the inner portion.

* * * * *